(12) United States Patent
Doe et al.

(10) Patent No.: US 10,527,535 B2
(45) Date of Patent: Jan. 7, 2020

(54) ROTARY RHEOMETER WITH DUAL READ HEAD OPTICAL ENCODER

(75) Inventors: Nigel Doe, Wilmington, DE (US); Peter Foster, Avondale, PA (US)

(73) Assignee: WATERS TECHNOLOGIES CORPORATION, Milford, MA (US)

(*) Notice: Subject to any disclaimer, the term of this patent is extended or adjusted under 35 U.S.C. 154(b) by 151 days.

(21) Appl. No.: 14/238,044

(22) PCT Filed: Aug. 3, 2012

(86) PCT No.: PCT/US2012/049474
§ 371 (c)(1),
(2), (4) Date: Feb. 10, 2014

(87) PCT Pub. No.: WO2013/025372
PCT Pub. Date: Feb. 21, 2013

(65) Prior Publication Data
US 2014/0208834 A1    Jul. 31, 2014

Related U.S. Application Data

(60) Provisional application No. 61/522,864, filed on Aug. 12, 2011.

(51) Int. Cl.
*G01N 11/14* (2006.01)

(52) U.S. Cl.
CPC ................. *G01N 11/14* (2013.01)

(58) Field of Classification Search
CPC ..................................... G01N 11/14
USPC ....................................... 73/54.28
See application file for complete search history.

(56) References Cited

U.S. PATENT DOCUMENTS

| 4,077,252 | A | 3/1978 | Stutz et al. |
| 432,287 | A | 10/1982 | Orth et al. |
| 4,352,287 | A | 10/1982 | Orth et al. |
| 4,516,177 | A * | 5/1985 | Moon .................. G11B 5/5521 360/77.02 |
| 6,031,223 | A | 2/2000 | Morishita |
| 6,167,752 | B1 | 1/2001 | Raffer |
| 7,526,941 | B2 | 5/2009 | Doe |
| 2004/0040166 | A1* | 3/2004 | Raab ...................... B23Q 35/04 33/503 |
| 2004/0111908 | A1* | 6/2004 | Raab ...................... B25J 18/002 33/503 |
| 2005/0199043 | A1 | 9/2005 | Doe et al. |

(Continued)

FOREIGN PATENT DOCUMENTS

GB    0 810 242 A    3/1959
GB    2 058 341 A    4/1981

(Continued)

OTHER PUBLICATIONS

International Search Report and Written Opinion for Application No. PCT/US2012/49474, dated Oct. 12, 2012, 7 pages.

(Continued)

*Primary Examiner* — Justin Seo
*Assistant Examiner* — Rodney T Frank
(74) *Attorney, Agent, or Firm* — Schmeiser, Olsen & Watts LLP (57) ABSTRACT

A rotary rheometer includes a drive shaft and a dual read head optical encoder that is configured to measure angular displacement or angular velocity of the drive shaft.

20 Claims, 8 Drawing Sheets

(56) References Cited

U.S. PATENT DOCUMENTS

| | | | |
|---|---|---|---|
| 2007/0193343 A1 | 8/2007 | Liberatore et al. | |
| 2007/0295055 A1 | 12/2007 | Doe | |
| 2009/0176261 A1* | 7/2009 | Williams | G01N 33/491 |
| | | | 435/13 |
| 2010/0269571 A1 | 10/2010 | Raffer | |

FOREIGN PATENT DOCUMENTS

| | | | |
|---|---|---|---|
| GB | 2 066 483 A | 7/1981 | |
| JP | 61-008618 A | 1/1986 | |
| JP | 07-140844 A | 6/1995 | |
| JP | 10-253398 A | 9/1998 | |
| JP | 11-108698 A | 4/1999 | |
| JP | 2000509502 A | 7/2000 | |

OTHER PUBLICATIONS

Extended European Search Report for Application No. 12823995.1, dated Feb. 9, 2015 (7 pages).

Japanese Office Action for Application No. 2014-525074, dated Jun. 21, 2016 (6 pages).

[No Author Listed] Signum™ DSi dual readhead rotary encoder system. Renishaw PLC, Jul. 2011, 7 pages, Data sheet, L-9517-9231-02-A.

Conde, L., et al., Low Cost Device for Precise Measurements of Dynamic Moduli in the Weissenburg Rheogoniometer. Journal of Rheology, vol. 31, pp. 527-535, 1987.

European Office Action for Application No. 12823995.1, dated Feb. 21, 2017 (5 pages).

Franck, A., Measuring and Evaluating Oscillation Data. TA Instruments, New Castle, 2008.

Haley, J.C., et al., Failure of time-temperature superposition in dilute miscible polymer blends. Colloid and Polymer Science 282.8 (2004): 793-801.

Japanese Search Report for Application No. 2014-525074, dated Jun. 15, 2016 (20 pages).

Kapoor, B., et al., Dynamic and extensional properties of starch in aqueous dimethylsulfoxide. Carbohydrate Polymers, vol. 42, Issue 4, Aug. 2000, pp. 323-335.

Kasehagen, L.J., et al., Rheology of long?chain randomly branched polybutadiene. Journal of Rheology 40.4 (1996): 689-709.

Merger, D., et al., Intrinsic nonlinearity from LAOStrain-experiments on various strain- and stress-controlled rheometers: a quantitative comparison. Rheol Acta (2014) 53:621-634, DOI 10.1007/s00397-014-0781-3.

Shaffer, E.O., et al., Relative molecular weight distributions of cis-polybenzoxazole/polyphosphoric acid rodlike liquid crystalline polymer solutions from dilute solution rheometry. Journal of Polymer Science Part B: Polymer Physics 30.3 (1992): 259-264.

* cited by examiner

ROTARY RHEOMETER WITH DUAL READ HEAD OPTICAL ENCODER

CROSS REFERENCE TO RELATED APPLICATION

This application is the National Stage of International Application No. PCT/US2012/049469, filed on Aug. 3, 2012, which claims priority to and benefit of U.S. Provisional Application No. 61/522,871, filed Aug. 12, 2011. The contents and teachings of each of these applications are hereby expressly incorporated herein by reference in their entirety.

TECHNICAL FIELD

This disclosure relates to the use of dual read head optical encoders in rotary rheometers.

BACKGROUND

Rotary rheometers, viscometers or viscosimeters are used to measure fluid or other properties of materials such as their viscosity by rotating, deflecting or oscillating a measuring object in a material, and measuring, for example, the torque required to rotate or deflect or oscillate the object within the material.

SUMMARY

The invention arises, in part, from the realization that a rheometer can be provided with a dual read head optical encoder for extended angular displacement resolution, elimination of displacement drift, and/or improved phase angle resolution.

In one aspect, the invention provides a rotary rheometer that includes a drive shaft and a dual read head optical encoder that is configured to measure angular displacement or angular velocity of the drive shaft.

Another aspect of the invention features a method that includes measuring angular displacement or angular velocity of a drive shaft of a rotary rheometer using a dual read head optical encoder.

Implementations may include one or more of the following features.

In some implementations, the dual read head optical encoder includes an encoder disk, a first read head, and a second read head. The encoder disk is connected to the drive shaft for rotation therewith. The first read head is configured to detect a relative position of the encoder disk. The second read head is also configured to detect the relative position of the encoder disk.

In certain implementations, the first and second read heads are disposed on opposing sides of the drive shaft.

In some implementations, the first and second read heads are configured such that drift in respective signals from the first and second read heads can be eliminated by taking an average of the two signals.

In certain implementations, measuring the angular displacement or angular velocity of the drive shaft includes receiving respective signals from the read heads, and taking an average of the two signals to eliminate drift in the signals.

As used herein, the term "rheometer" shall mean rheometers, viscometers, viscosimeters and similar instruments that are used to measure the properties of fluid or similar materials.

The term "measuring object" shall mean an object having any one of several geometries, including, for example, cones, discs, vanes, parallel plates, concentric cylinders and double concentric cylinders.

Implementations can provide one or more of the following advantages.

In some implementations, a rotary rheometer is provided with extended angular displacement resolution.

In certain implementations, drift in a signal representing displacement of a drive shaft of a rotary rheometer is eliminated.

In some implementations, a rotary rheometer is provided with improved phase angle resolution.

Other aspects, features, and advantages are in the description, drawings, and claims.

BRIEF DESCRIPTION OF THE DRAWINGS

Like reference numbers indicate like elements.

DETAILED DESCRIPTION

Figure 1:
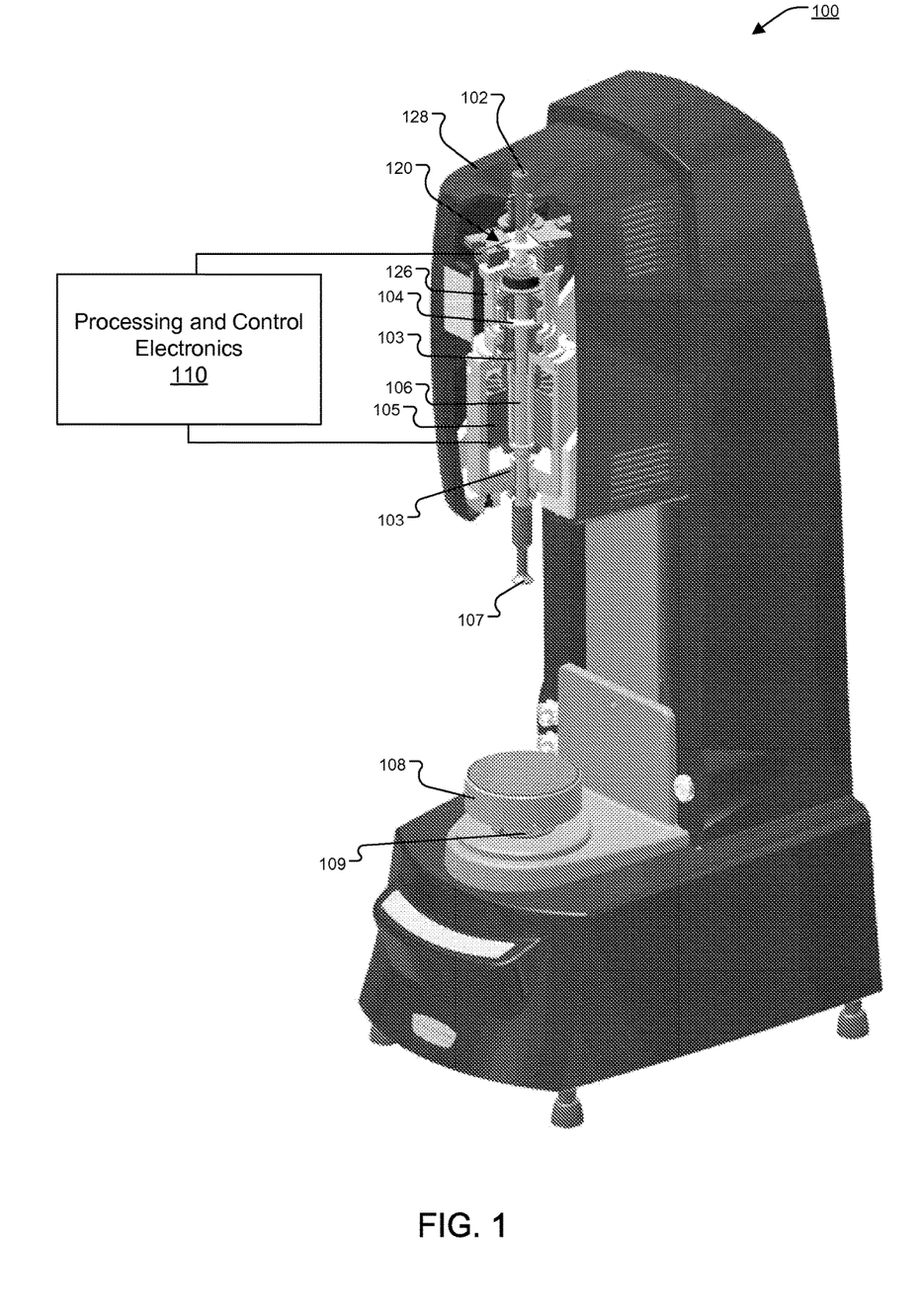
FIG. 1 is a schematic perspective view of a rotary rheometer.

FIG. 1 is a schematic perspective view of a rotary rheometer 100, showing a draw rod 102, air bearings 103, a magnetic thrust bearing 104, drag cup motor 105, drive shaft 106, a first measuring object 107, a second measuring object 108, a normal force transducer 109, and processing and control electronics 110. The drag cup motor 105 contains a current in its coils to generate and apply a torque to the drive shaft 106. The torque in the drive shaft 106, in turn, applies torque to the first measuring object 107. The amount of torque applied depends on the current applied to the drag cup motor so the rheometer 100 measures the motor torque from the energy input to the drag cup motor 105.

The processing and control electronics 110 are in communication with the drag cup motor 105 and are configured to monitor the torque by monitoring the current applied to the drag cup motor 105. The processing and control electronics 110 can include an assembly of at least one type of device that is programmable or capable of receiving inputted data, storing data, performing calculations, or displaying data. The processing and control electronics 110 may be equipped with an algorithm to calculate different rheological properties, such as viscosity. The processing and control electronics 110 may also include motion control electronics, e.g., for controlling drag cup motor 105.

Notably, the rheometer 100 is provided with a dual read head optical encoder 120. The dual read head optical encoder 120 is in communication with the processing and control electronics 110 and is capable of measuring an angular displacement or angular velocity of the drive shaft 106.

Figure 2:
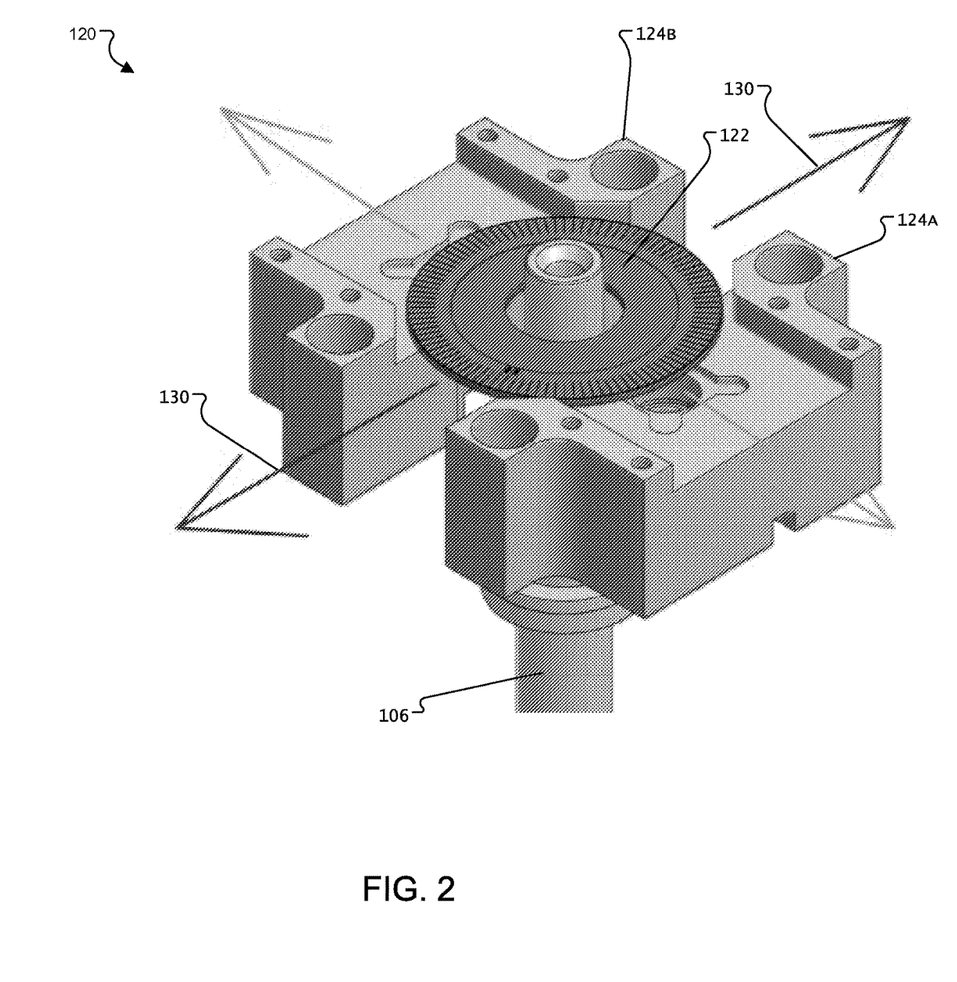
FIG. 2 is schematic perspective view of a dual read head optical encoder from the rotary rheometer of FIG. 1.

Referring to FIG. 2, the dual read head optical encoder 120 includes an encoder disk 122 that is connected to and rotates with the drive shaft 106. The dual read head optical encoder 120 also includes first and second read heads 124A, 124B, which are disposed opposite each other about the drive shaft 106. In this regard, the read heads 124A, 124B can be mounted to the structure surrounding the drive shaft 106 such as a casing 126 (FIG. 1) enclosing the thrust bearing 104 and/or the outer housing 128 that encloses the drag cup motor 105 and bearings 103, 104. The read heads 124A, 124B each include a light source and photo detector array for reading an optical pattern that corresponds to the position of the encoder disk 122 relative to the read heads 124A, 124B. The use of dual read heads can provide for improved resolution (e.g., better than 2 nanoradians), enhanced phase resolution, reduced drift, and/or reduction in noise.

Figure 3:
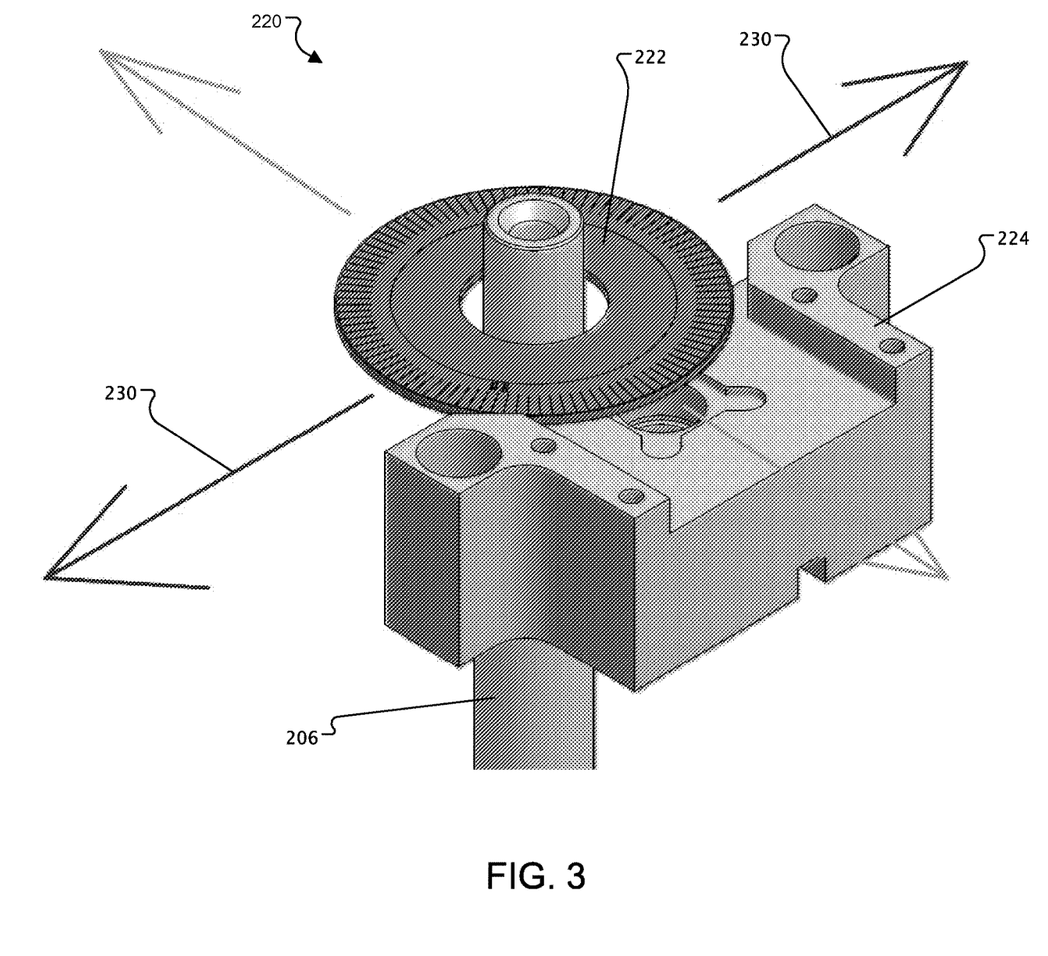
FIG. 3 is schematic perspective view of a conventional single read head optical encoder.

By comparison, FIG. 3 illustrates a conventional single read head optical encoder 220, which has a similar construction to the optical encoder 120 of FIG. 2, with the exception being that only a single read head 224 is provided for reading an encoder disk 222. A shown in FIG. 3, the single read head 224 is arranged along one side of a drive shaft 206 of a rotary rheometer. Due to this arrangement, movement of the drive shaft 206 along the plane illustrated by arrows 230 is observed by the single read head 224 as displacement. Because no system is infinitely stiff, the slightest movement of the drive shaft 206 in the direction away from the read head 224 along arrows 230 can limit absolute measurable resolution and can lead to more noise (error) in phase and displacement, and can be subject to drift over time.

In contrast, with the dual read head optical encoder 120 of FIG. 2, horizontal movement in the plane 130 is observed as displacement by the first read head 124A, and the second read head 124B observes the same horizontal movement as a displacement equal in magnitude and opposite direction. The average of these two measurements will cancel out the horizontal movement.

Figure 4A:
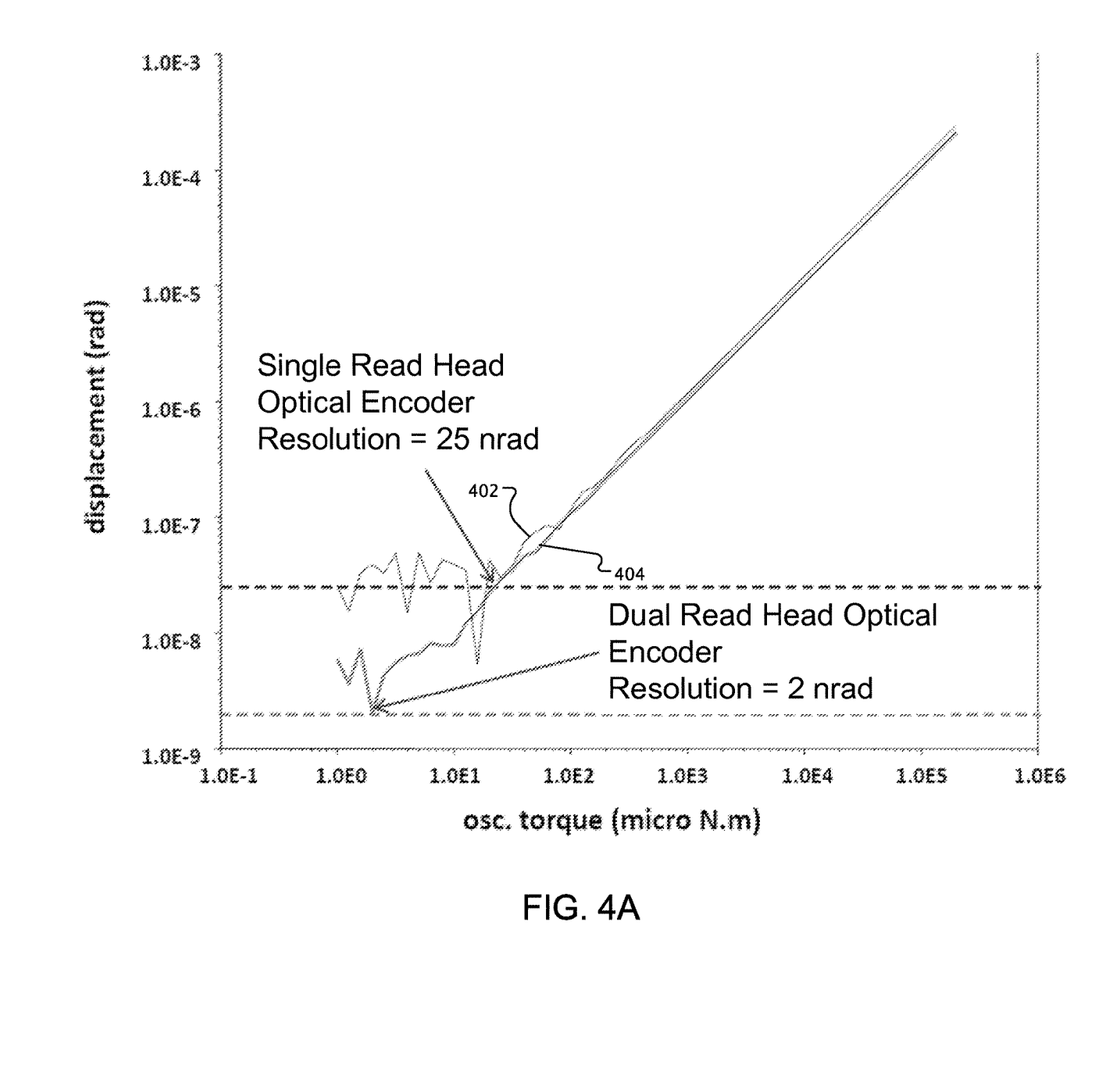
FIGS. 4A through 4E are test data showing the improved performance of a rheometer using the dual read head optical encoder of FIG. 2, compared to a rheometer using the conventional single read head optical encoder of FIG. 3.

The improved performance provided by a rheometer with the dual read head optical encoder 120 of FIG. 2, compared to a rheometer with the conventional single read head rotary encoder 220 is shown in FIGS. 4A-4E. FIG. 4A is a plot of displacement (in radians) over oscillatory torque (in micro Newton meters) as measured by the conventional single read head optical encoder (line 402) and as measured by the dual read head optical encoder (line 404). The single read head optical encoder provides resolution of 25 nanoradians, and the dual read head optical encoder provides resolution of 2 nanoradians—better than 10× improvement in resolution.

Figure 4B:
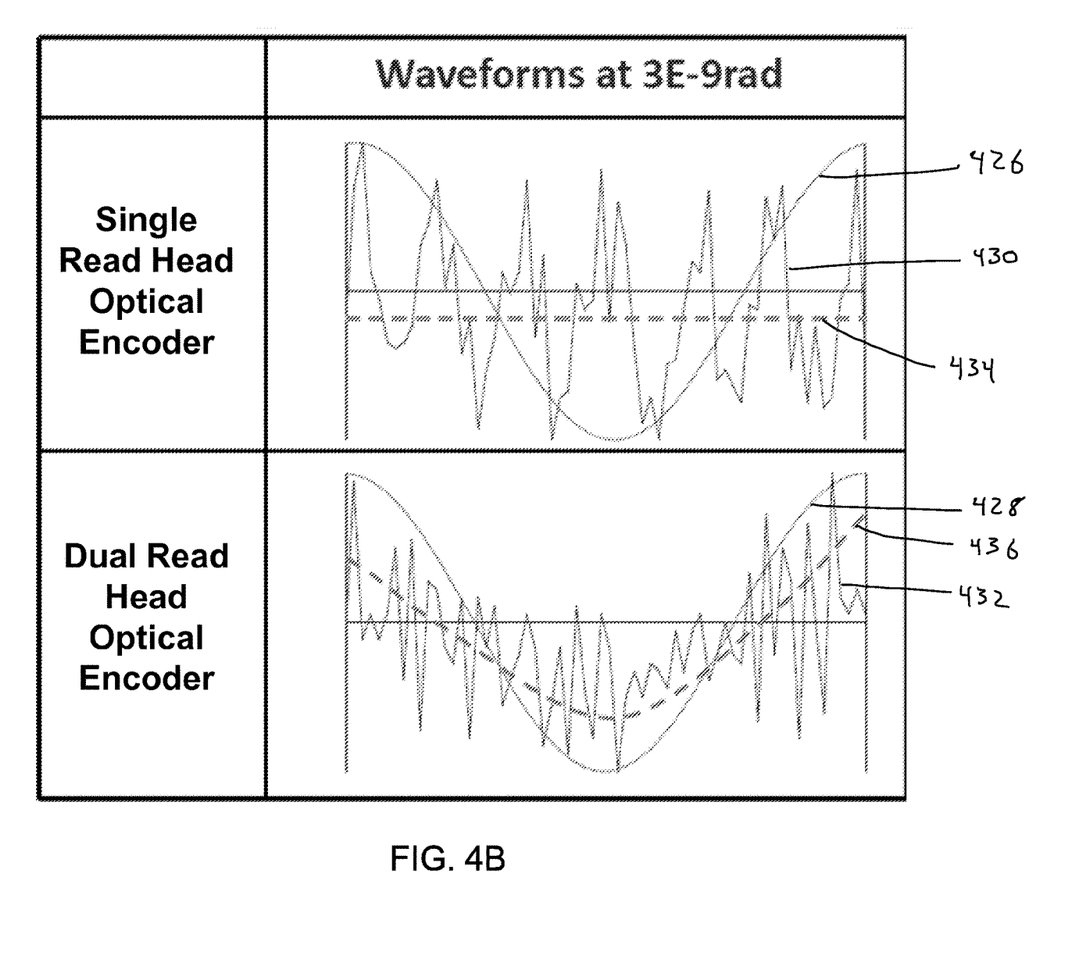

FIG. 4B shows displacement signal waveforms at $3 \times 10^{-9}$ radians for the single encoder reader and for the dual encoder reader. More specifically, FIG. 4B shows amplitudes of torque (lines 426, 428) applied by the rheometer motor to the drive shaft and measured displacements (lines 430, 432) of a sample over time for both a single and a dual read head optical encoder. Also shown are lines of best fit (lines 434, 436) for the measured displacements in each case. As can be seen, a waveform is not discernable in the displacement signal for the single read head optical encoder, whereas the same is not true for the dual read head optical encoder. The dual read head optical encoder can make oscillation measurements down to much smaller deformation.

Figure 4C:
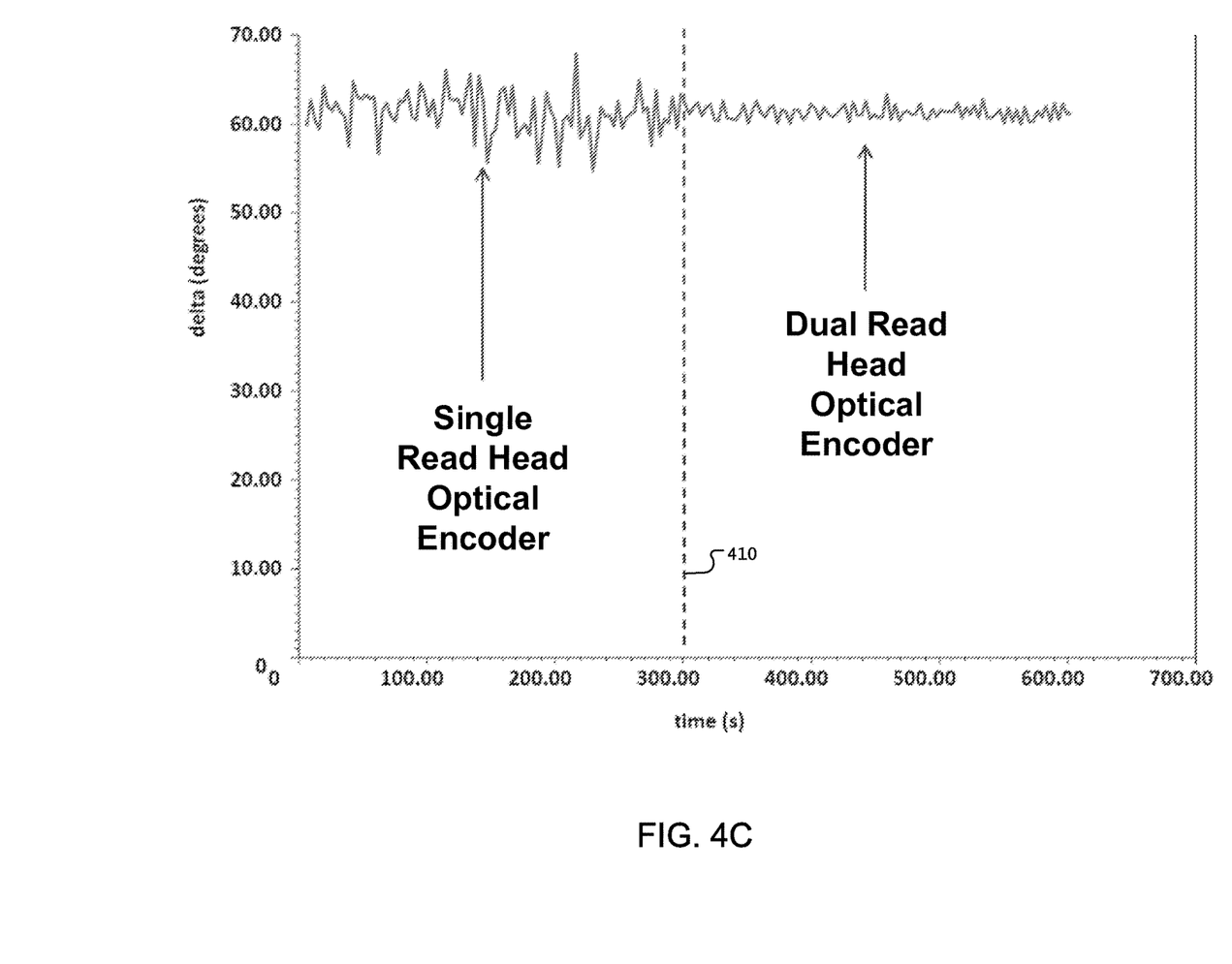

FIG. 4C illustrates how the dual read head optical encoder also provides enhanced phase angle resolution in oscillatory measurements. Phase angle is a measure of time relation between applied torque and measured sample displacement. Sample material properties govern any delay between applied torque and sample displacement, thus phase angle is important to rheology in addition to displacement. By way of example, the line of best fit 436 in FIG. 4B appears aligned with torque waveform 428, i.e., a low phase angle. Depending upon a sample's material properties, however, the measured displacement 432 and corresponding line of best fit 436 could be shifted horizontally relative to the applied torque waveform 428, i.e., a higher phase angle. Returning to FIG. 4C, the signal for the measured phase angle for the single read head optical encoder is shown to the left of line 410 (time 300 seconds) and the signal for the measured phase angle for the dual read head optical encoder is shown to right of line 410. The dual read head optical encoder provides for 3× less noise by comparison.

Figure 4D:
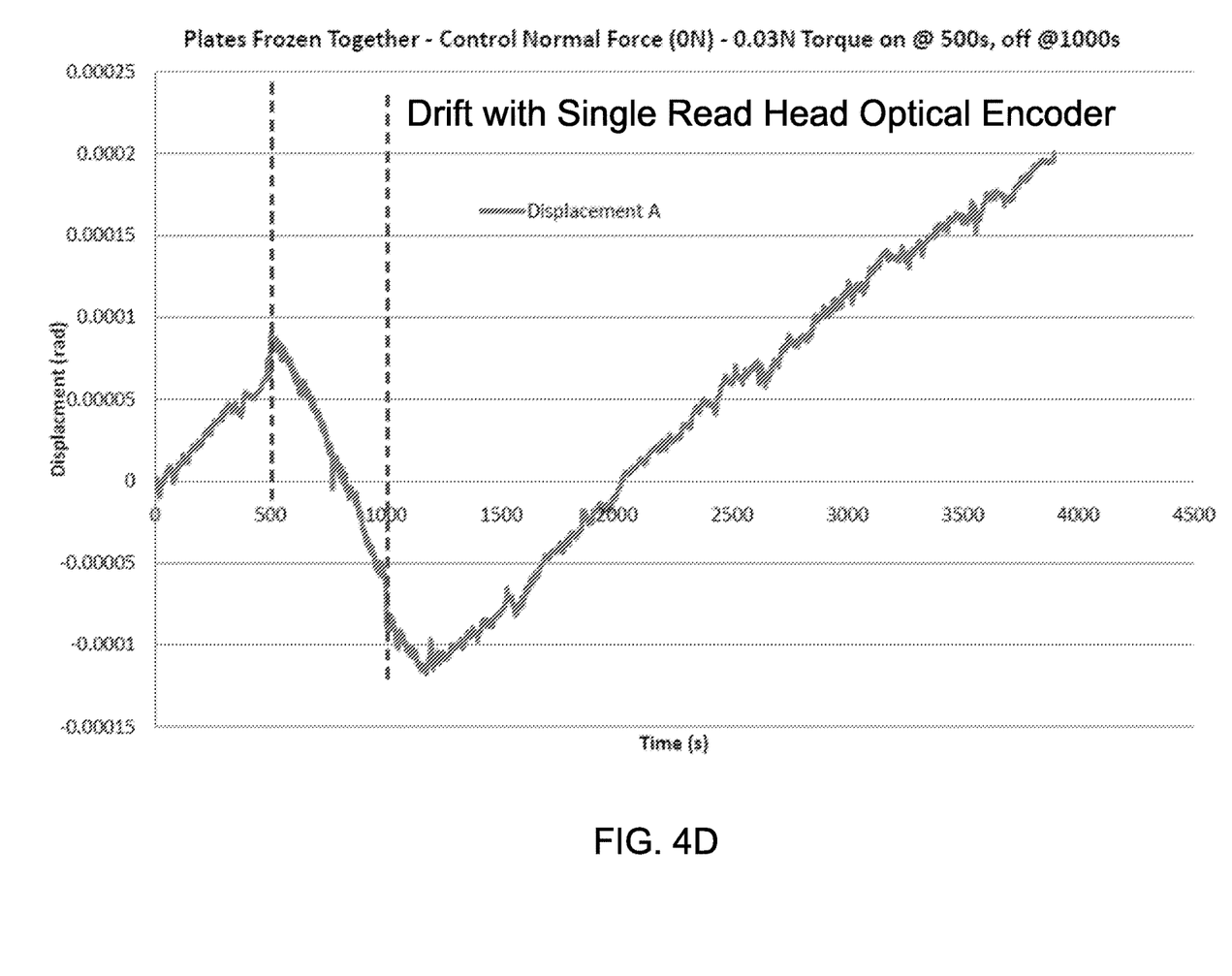
Figure 4E:
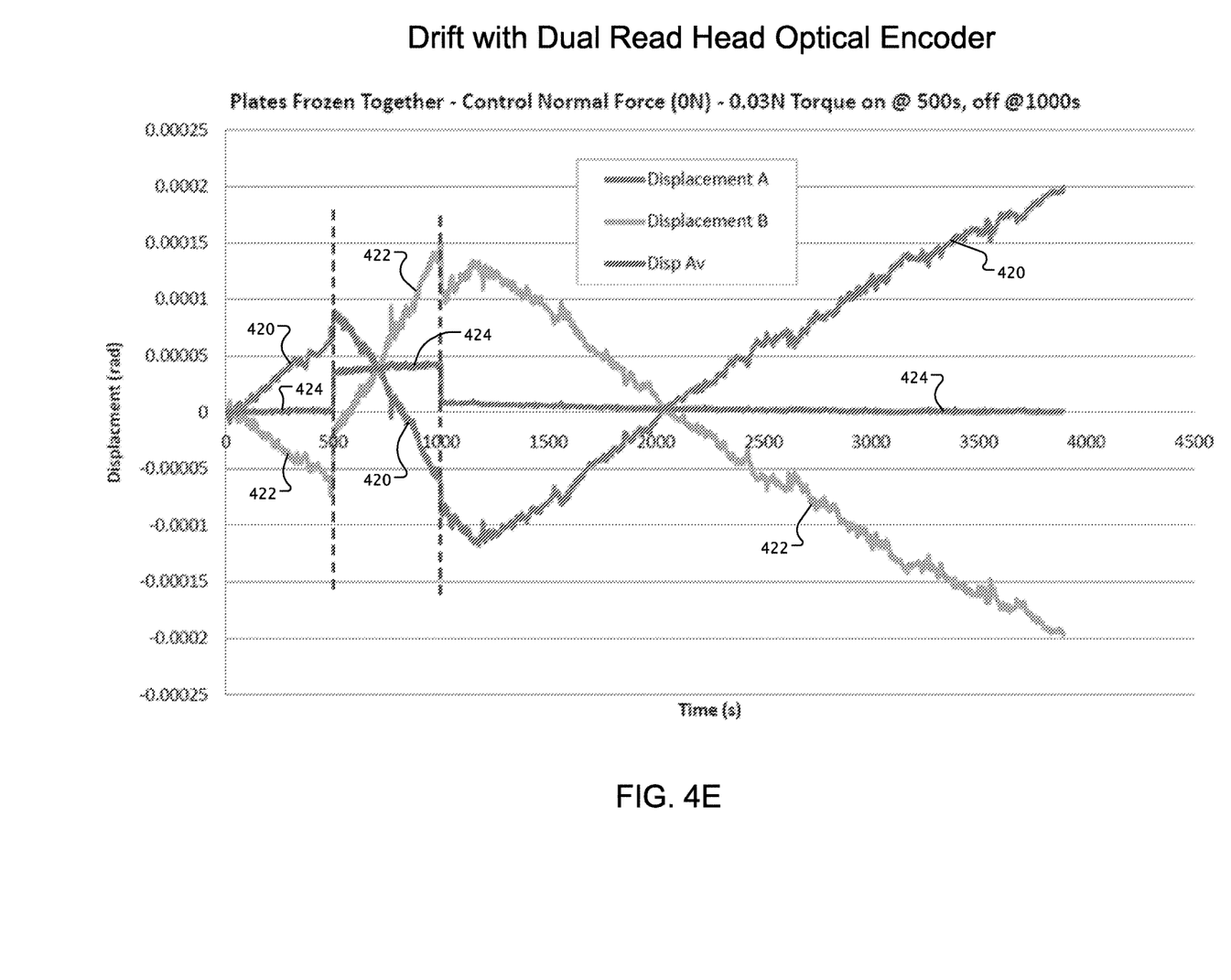

FIGS. 4D and 4E are plots illustrating the displacement drift associated with a rigid sample as measured by the single read head optical encoder and by the dual read head optical encoder, respectively. As can be seen in FIG. 4D, with a rigid sample, displacement signal can drift with time. The magnitude and direction of drift will depend on many factor including temperature, deformation conditions, torque and normal force, sample, environment, etc. Referring to FIG. 4E, line 420 represents the displacement signal for the first read head 124A, line 422 represent the displacement signal for the second read head 124B, and line 424 represents an average of the two signals 420 and 422. As can be seen in FIG. 4E, drift will still occur with each read head of the dual read head optical encoder. However, with the dual read head optical encoder, the drift can be eliminated by taking the average of the two signals from the read heads 124A, 124B.

Although one or more implementations have been described in detail above, other modifications are possible. Accordingly, other implementations are within the scope of the following claims.

What is claimed is:

1. A rotary rheometer comprising:
   a drive shaft positioned between a first read head and a second read head for detecting a relative position of an encoder disk;
   a dual read head optical encoder including the encoder disk; and
   wherein the first read head and the second read head are disposed on opposing sides of the drive shaft, the dual read head optical encoder being configured to measure angular displacement or angular velocity of the drive shaft.

2. The rotary rheometer of claim 1, wherein the drive shaft is mounted vertically and coupled to a housing at an upper end thereof and to a first measuring object at a lower end thereof.

3. The rotary rheometer of claim 1, further comprising a magnetic thrust bearing disposed around the drive shaft below the dual read head optical encoder.

4. The rotary rheometer of claim 3, further comprising:
   a first air bearing disposed around the drive shaft below the magnetic thrust bearing; a drag cup motor disposed around the drive shaft below the first air bearing; and a second air bearing disposed around the drive shaft below the drag cup motor.

5. The rotary rheometer of claim 1, further comprising a normal force transducer coupled to a second measuring object.

6. The rotary rheometer of claim 1, wherein the encoder disk is connected to the drive shaft for rotation therewith.

7. The rotary rheometer of claim 1, wherein the first and second read heads are mounted to a structure surrounding the drive shaft and the drive shaft extends through both the first and second read heads and the encoder disk.

8. The rotary rheometer of claim 1, wherein the dual read head optical encoder is in communication with processing and control electronics and measures at least one of an angular displacement and an angular velocity of the drive shaft, and the processing and control electronics apply an algorithm to calculate a rheological property of a material based on the measured at least one of the angular displacement and the angular velocity of the drive shaft and at least one of: (i) limited error in phase angle measurement which provides an enhanced phase angle resolution, (ii) limited error in displacement measurements, and (iii) eliminated drift of a displacement signal over time provided by the dual read head optical encoder.

9. The rotary rheometer of claim 1, wherein the first read head measures a movement of the drive shaft of the rotary rheometer in a first direction as a displacement.

10. The rotary rheometer of claim 9, wherein the second read head measures the movement of the drive shaft as a displacement equal in magnitude to the displacement measured by the first read head but in a second direction opposite the first direction.

11. The rotary rheometer of claim 10, wherein an average of the measurements from the first read head and the second read head cancel out the movement.

12. The rotary rheometer of claim 11, wherein cancelling out the movement limits error in phase angle measurement to provide an enhanced phase angle resolution.

13. The rotary rheometer of claim 11, wherein cancelling out the movement limits error in displacement measurements.

14. The rotary rheometer of claim 11, wherein cancelling out the movement eliminates a drift of a displacement signal over time.

15. The rotary rheometer of claim 1, further comprising:
a first measuring object disposed at an end of the drive shaft and configured to contact a sample.

16. The rotary rheometer of claim 15, further comprising:
a second measuring object coaxially aligned with and spaced apart from the drive shaft and configured to contact an opposite side of the sample as the first measuring object.

17. The rotary rheometer of claim 1, wherein the rotary rheometer is configured to apply an oscillatory torque to the drive shaft.

18. The rotary rheometer of claim 17, wherein the rotary rheometer is configured to utilize the dual read head optical encoder to provide an enhanced phase angle resolution comparing timing of applied torque to measured displacement of the sample.

19. A method comprising: measuring at least one of angular displacement and angular velocity of a drive shaft of a rotary rheometer with a dual read head optical encoder, the drive shaft positioned between a first read head and a second read head, wherein the first read head and the second read head are disposed on opposing sides of the drive shaft and the first read head measures a movement of the drive shaft of the rotary rheometer in a first direction as a displacement and a second read head measures a movement of the drive shaft as a displacement equal in magnitude to the displacement measured by the first read head but in a second direction opposite the first direction.

20. The method of claim 19, wherein an average of the measurements from the first read head and the second read head cancel out the movement which at least one of: (i) limits error in phase angle measurement to provide an enhanced phase angle resolution, (ii) limits error in displacement measurements, and (iii) eliminates a drift of a displacement signal over time.

* * * * *